US010232167B2

(12) United States Patent
Nazareth et al.

(10) Patent No.: US 10,232,167 B2
(45) Date of Patent: Mar. 19, 2019

(54) ELECTRODE CONSTRUCTION FOR IMPLANTABLE MEDICAL ELECTRICAL LEADS

(71) Applicant: Medtronic, Inc., Minneapolis, MN (US)

(72) Inventors: Vishal R Nazareth, St. Louis Park, MN (US); Gregory A Boser, Richfield, MN (US); Lorraine R Gaunt, Albertville, MN (US)

(73) Assignee: Medtronic, Inc., Minneapolis, MN (US)

( * ) Notice: Subject to any disclaimer, the term of this patent is extended or adjusted under 35 U.S.C. 154(b) by 546 days.

(21) Appl. No.: 14/521,958

(22) Filed: Oct. 23, 2014

(65) Prior Publication Data

US 2015/0320995 A1 Nov. 12, 2015

Related U.S. Application Data

(60) Provisional application No. 61/989,830, filed on May 7, 2014.

(51) Int. Cl.
*A61N 1/00* (2006.01)
*A61N 1/05* (2006.01)

(52) U.S. Cl.
CPC ............ *A61N 1/05* (2013.01); *A61N 1/0563* (2013.01); *A61N 1/0565* (2013.01); *A61N 1/056* (2013.01); *Y10T 29/49206* (2015.01)

(58) Field of Classification Search
CPC ... A61N 1/04; A61N 1/05; A61N 1/36; A61N 1/362; A61N 1/042; A61N 1/0436; A61N 1/0565; A61N 1/056; A61N 1/0563; Y10T 29/49206

See application file for complete search history.

(56) References Cited

U.S. PATENT DOCUMENTS

| | | | |
|---|---|---|---|
| 4,440,178 A | 4/1984 | Bussard et al. | |
| 4,674,009 A | 6/1987 | Wong | |
| 5,849,031 A | 12/1998 | Martinez et al. | |
| 5,931,864 A * | 8/1999 | Chastain et al. | 607/128 |
| 6,501,992 B1 | 12/2002 | Belden et al. | |
| 7,047,082 B1 | 5/2006 | Schrom et al. | |
| 7,340,305 B2 | 3/2008 | Fishbach et al. | |

(Continued)

OTHER PUBLICATIONS (PCT/US2013/064824) PCT Notification of Transmittal of the International Search Report and the Written Opinion of the International Searching Authority.

(Continued)

*Primary Examiner* — George Manuel

(57) ABSTRACT

An implantable electrode for electrical stimulation of a body, for example, being a component of an implantable medical electrical lead, is preferably in the form of a coiled conductor wire, wherein the wire is formed by a tantalum (Ta) core directly overlaid with a platinum-iridium (Pt—Ir) cladding. When a maximum thickness of the Pt—Ir cladding defines a cladded zone between an outer, exposed surface of the electrode and the Ta core, a surface of the Ta core encroaches into the cladded zone by no more than approximately 50 micro-inches. The tantalum core may be cold worked to improve surface quality or formed from a sintered and, preferably, grain stabilized tantalum.

9 Claims, 4 Drawing Sheets

(56) References Cited

U.S. PATENT DOCUMENTS

| | | |
|---|---|---|
| 7,612,291 B2 * | 11/2009 | Chastain et al. ........... 174/126.1 |
| 7,702,387 B2 | 4/2010 | Stevenson et al. |
| 7,887,681 B2 | 2/2011 | Zhou |
| 7,930,038 B2 | 4/2011 | Zarembo |
| 8,131,369 B2 | 3/2012 | Taylor et al. |
| 2004/0064175 A1 | 4/2004 | Lessar et al. |
| 2006/0193889 A1 | 8/2006 | Spradlin et al. |
| 2007/0265692 A1 | 11/2007 | Koop et al. |
| 2010/0211147 A1 | 8/2010 | Schiefer et al. |
| 2011/0027453 A1 * | 2/2011 | Boock et al. ................ 427/2.12 |

OTHER PUBLICATIONS

"There's only one thing tantalum can't do: Give up.", Sep. 26, 2012, 15 pp, www.plansee.com.

* cited by examiner

ELECTRODE CONSTRUCTION FOR IMPLANTABLE MEDICAL ELECTRICAL LEADS

CROSS-REFERENCE TO RELATED APPLICATIONS

This application claims the benefit of U.S. Provisional Application No. 61/989,830, filed on May 7, 2014. The disclosure of the above application is incorporated herein by reference in its entirety.

FIELD OF THE DISCLOSURE

The present disclosure pertains to implantable medical electrical leads, and more particularly to electrode constructions thereof.

BACKGROUND

Implantable medical systems that are designed to deliver electrical stimulation, for example, to cardiac muscle or the spinal cord, and/or to monitor bodily electrical activity, typically include a relatively compact implantable device to which one or more elongate implantable electrical leads are coupled, for example, like the exemplary prior art system 10 schematically shown in FIG. 1A. FIG. 1A illustrates system 10 including an implantable defibrillator device 500 and a defibrillation lead 100, which is connected to device 500 and extends transvenously therefrom, into a heart of a patient, such that a defibrillation electrode 11 and a pace-sense electrode 13 of lead 100 are located in the right ventricle of the heart. Those skilled in the art appreciate that a power source and circuitry of device 500 are contained in a hermetically sealed housing 55 of device 500, which housing 55, being formed from a conductive metal such as titanium, may function as an electrode, in concert with electrode 11, to deliver high voltage pulses for defibrillation therapy in response to a cardiac arrhythmia, for example, sensed by electrodes 13, 11.

With reference to FIG. 1B, an outer insulation sheath 12 of lead 100 contains a first elongate conductor 20 that couples electrode 11 to a contact 151 of a connector terminal 15 of lead 100, and a second elongate conductor 135, which is isolated from first conductor 20 and couples electrode 13 to a contact pin 153 of terminal 15. FIG. 1A further illustrates device 500 including a connector module 51 that has a port 501 into which connector terminal 15 is inserted for electrical coupling with the circuitry contained in housing 55, for example, via electrical contacts, which are mounted within port 501 and coupled to the circuitry via hermetically sealed feedthroughs. Suitable constructions for such a connector module and lead connector are known to those skilled in the art.

With further reference to FIGS. 1A-B, electrode 11 is shown formed by a coiled conductor wire, which may be an exposed distal portion of conductor 20 or a separately formed coil coupled to conductor 20, for example, by a weld or a crimp joint. Such electrodes were at one time made entirely of from a platinum-iridium alloy (Pt—Ir), since Pt—Ir provides an effective bio-stable, bio-compatible, and corrosion-resistant electrode surface interface. More recently, in order to reduce costs, such coil electrodes have been made of a composite structure employing a tantalum core provided with an overlay or cladding of platinum-iridium. One such construction is disclosed in U.S. patent application Ser. No. 13/664,782, filed Oct. 31, 2012 by Boser, et al. and incorporated herein by reference in its entirety.

SUMMARY

Embodiments of the present invention pertain to electrode constructions in which a tantalum (Ta) core is overlaid with a Pt—Ir cladding. Preferred embodiments of electrodes are preferably in the form of a coiled conductor wire, wherein the wire includes a Ta core and a Pt—Ir cladding directly overlaying the core and forming an exposed outer surface of the electrode. A cladded zone, between the exposed outer surface and the Ta core, may be defined by a maximum thickness of the Pt—Ir cladding.

Platinum alloy clad tantalum defibrillation coils can constitute a substantial portion of the manufacturing cost of an implantable defibrillation electrode. A signification portion of this cost lies in the use of precious raw materials such as platinum. One of the challenges has been the ability to further thin the outer Pt—Ir cladding. One reason for this difficulty lies in the surface roughness of available tantalum wires. The cited Boser application addresses this aspect of the invention by reducing the surface roughness of the tantalum core wire, believed to be caused by the large grain size of the core wire. One process disclosed in the Boser application requires additional processing of a melt quality tantalum core wire such as UNS R05200 to reduce grain size and/or smooth the wire surface, which adds cost and complexity. The smoothing of the surface of the core wire reduces the mechanical inter-lock between the core wire and the cladding, which affects its mechanical properties. An alternative as discussed in the Boser application is the use of a sintered quality tantalum core that has reduced grain size to start with, for example a sintered and grain stabilized Ta rod ((UNS R05400) as produced by PLANSEE SE of Austria (www.plansee.com), that has reduced grain size to start with but a higher cost.

The present invention provides a low cost defibrillation lead by reducing the thickness of the Pt—Ir cladding compared to prior art leads. In particular, the present invention provides a defibrillation lead having a melted quality tantalum core wire such as UNS R0520 and a Pt—Ir cladding in the 1-3 micron range, preferably approximately one micron.

The process for constructing the coil electrode does not require smoothing of the surface of the core wire, so cost and complexity is kept to a minimum. Additionally, the resultant composite structure displays superior mechanical characteristics.

The invention is practiced employing a cladding technique provided by Anomet, Inc. Shrewsbury, Mass. (www.anometproducts.com) to fabricate the wires used to form these electrodes. Unlike the current traditional DFT approach, the inventors understand that Anomet wraps a foil around a core to form the cladding, extruding the clad core within in a nickel/stainless steel outer layer and then etching off the outer layer and drawing the cladded core to finished size. This process as applied to a melt quality tantalum core wire is particularly beneficial in the context of a coiled wire defibrillation electrode as in the present invention. The resultant clad wires can be obtained from Anomet, Inc.

In the specific context of a defibrillation electrode, the approach of coated wires provided by Anomet using this cladding technique have several benefits. First, it enables thinning of the platinum cladding down to about 1 micron without exposing the melted quality tantalum core (e.g. R05200).

Second, as noted above, one of the primary limitations with thinning the Pt—Ir. cladding has been the rough surface of melt quality tantalum core wires. This does not appear to be a concern when applying the cladding using the Anomet processing route. The surface of the melt quality tantalum stock does not need to be modified or smoothed prior to application of the cladding as described in the Boser application. Melt quality tantalum core wires that have not undergone such processing prior to application of the cladding materials are referred to hereafter as "un-smoothed". The ability to use such un-smoothed core wires is believed to provide a significant advantage.

Third, the resultant composite wire displays improved rotary bend fatigue performance. The inventors have determined that the composite wire has a significantly higher endurance limit by about 20 ksi when compared with Medtronic's current commercialized tantalum cored defibrillation coil wires, while having lower variability resulting in better predictability. EBSD analysis has shown microstructural textural difference between the two wires. This along with the absence of surface silica inclusions as observed are believed to be some of the significant factors that contribute to its improved fatigue performance of the composite defibrillation coil wire of the invention.

Fourth, no buckling has been observed during coiling. Such buckling or wrinkling has been observed on other conductors having a smoother interface, believed due to the lack of mechanical interlocking. The use of un-smoothed melt quality tantalum cores is believed to be directly related to this improved performance.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals/letters denote like elements.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives. Examples of constructions, materials, dimensions and fabrication processes are provided for select elements and all other elements employ that which is known by those skilled in the art.

Figure 1A:
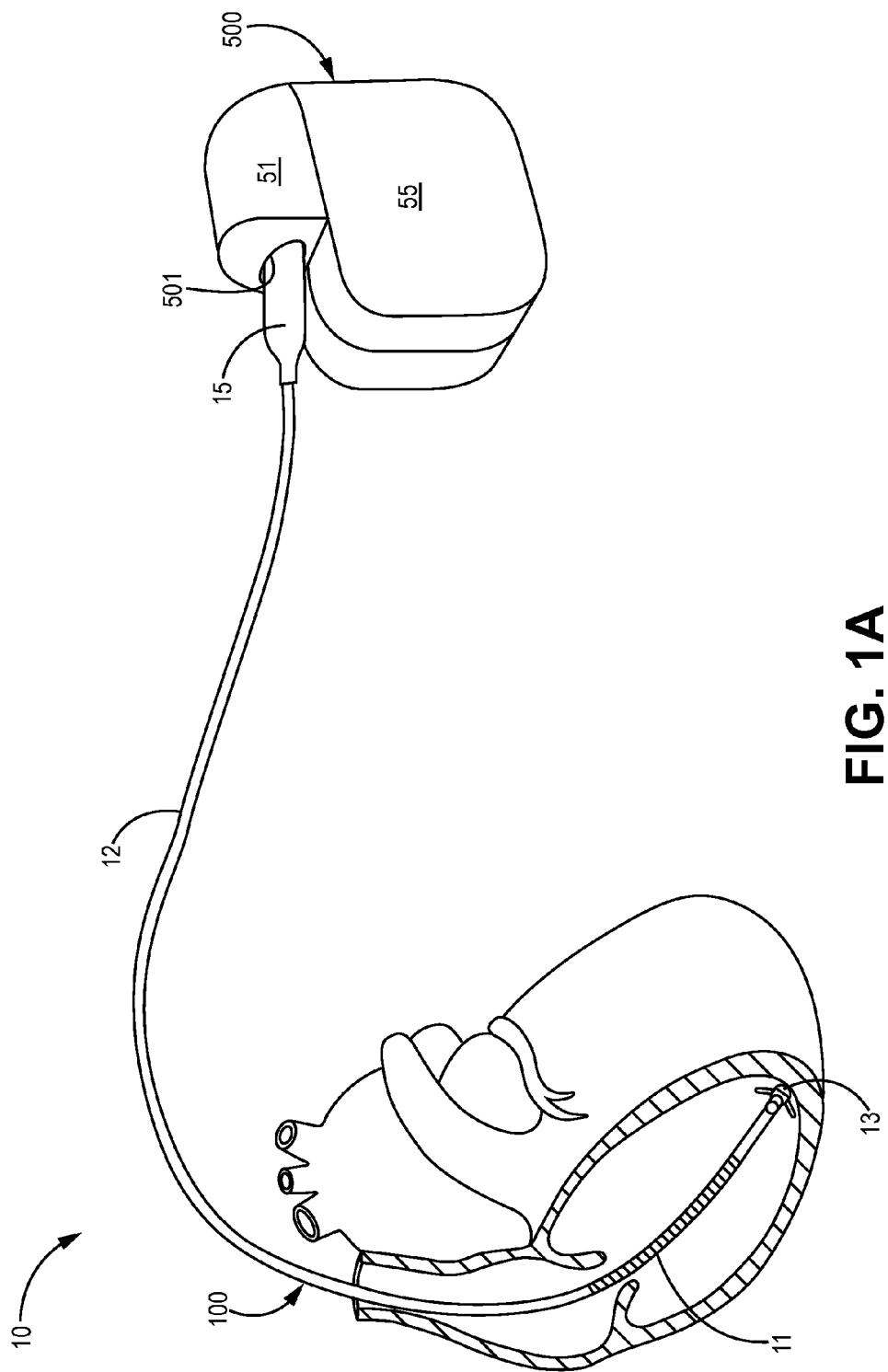
FIG. 1A is a schematic depicting an exemplary implantable medical system.
Figure 1B:
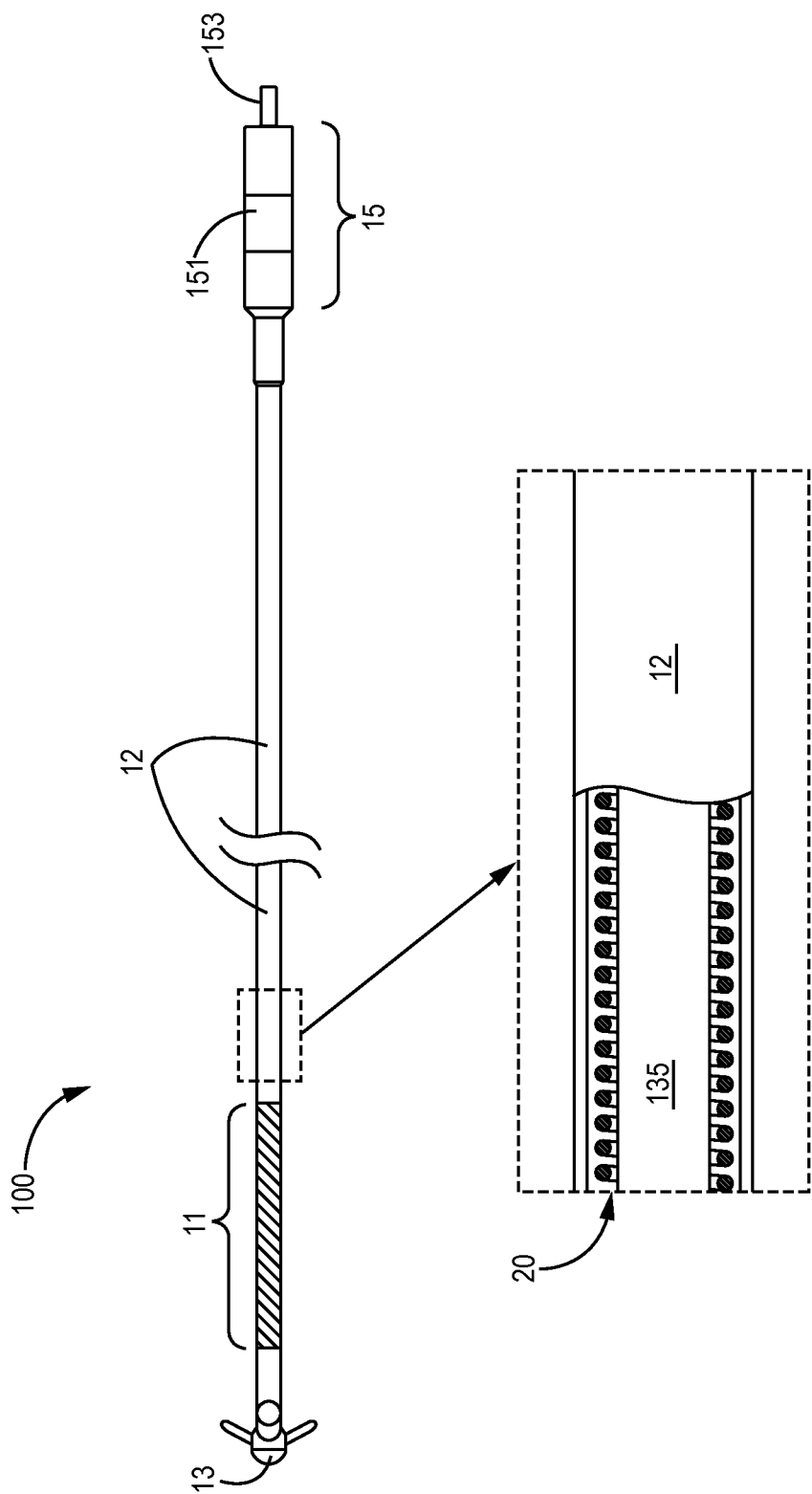
FIG. 1B is a plan view, with an enlarged cut-away cross-section, of an implantable medical electrical lead, which may include an electrode constructed according to some embodiments of the present invention.

FIG. 1B is a plan view, with an enlarged cut-away cross-section, of implantable medical electrical lead 100. Electrode 11 is preferably formed by an exposed distal portion of conductor coil 20, which extends distally out from insulation sheath 12. Alternately, electrode 11 is formed from a separate member, for example, another coiled conductor wire, which is coupled to conductor coil 20 for example, by a crimp joint and/or a weld joint, according to methods known in the art. One or more conductor wires, which are coiled to form electrode 11 have an exposed outer surface formed by a Pt—Ir cladding that overlays a Ta core. This composite type wire is formed as a drawn-filled-tube (DFT®) by a cold-drawn process known to those skilled in the art.

Figure 2:
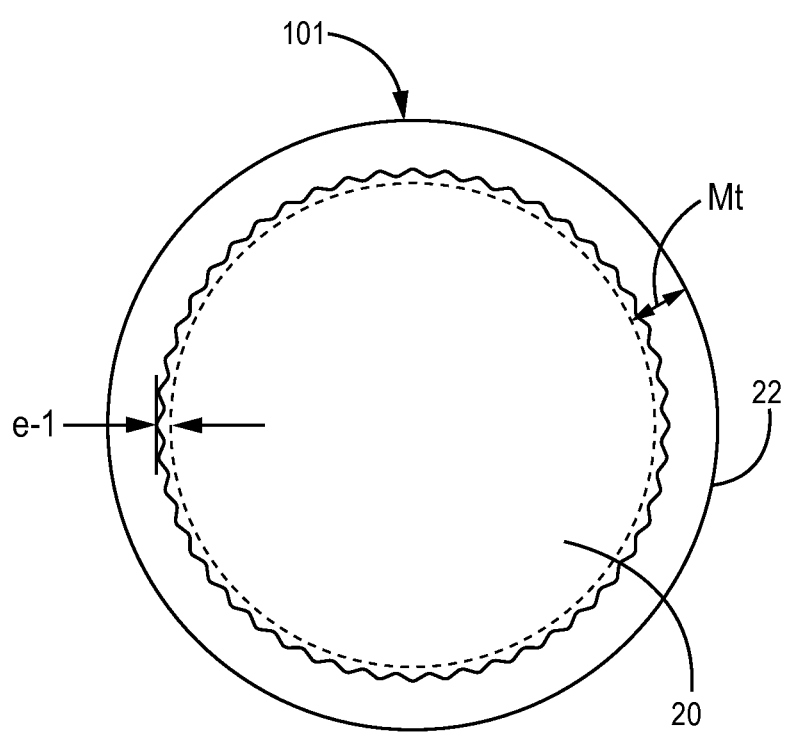
FIG. 2 is a cross-section view of a prior art Pt—Ir cladded conductor wire.

FIG. 2 is a cross-sectional view of a prior art conductor wire 101, which includes a Ta core 20 overlaid by a Pt—Ir cladding 22. FIG. 2 illustrates cladding 22 having a maximum thickness Mt of approximately 500 to 600 micro-inches (0.0005-0.0006 inch), which defines a cladded zone of wire 101. The inner perimeter of the cladded zone is designated with a dashed line. FIG. 2 further illustrates core 20 having a surface roughness that encroaches into the cladded zone, for example, by a distance e-1, which may be as large as between approximately 200 to 300 micro-inches. Because such an encroachment of core Ta-1 causes a minimum thickness of cladding 22 to be significantly smaller than the maximum thickness Mt, specification of an increased nominal cladding thickness for wire 101 may be necessary to meet a minimum wall thickness requirement for cladding 22. The specification of increased nominal Pt—Ir cladding thickness is contrary to a desired reduction in cladding thickness that can translate into cost savings, and may facilitate a reduction in the profile of electrodes, such as electrode 11, for example, by allowing the winding of a smaller diameter coil.

Figure 3:
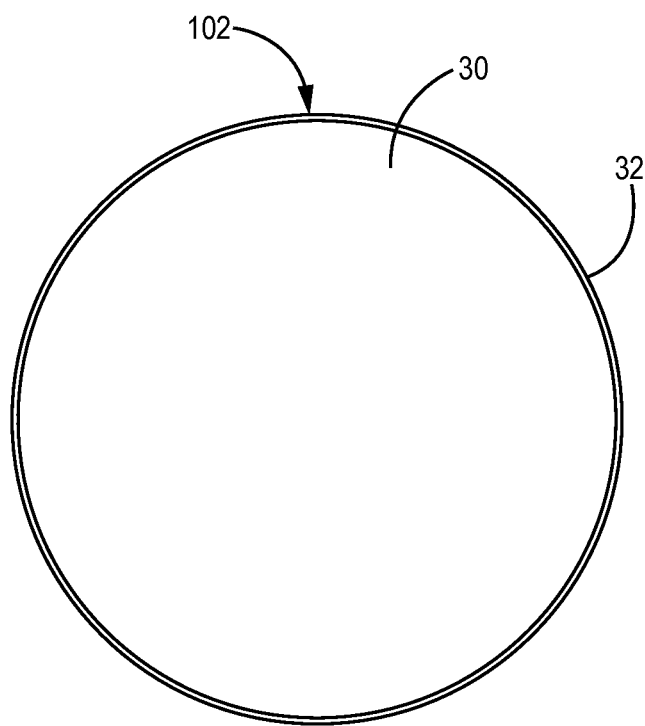
FIG. 3 is a cross-section views of a Pt—Ir cladded conductor wire according to the present invention.

FIG. 3 is a cross-sectional views of a conductor wire 102 which includes a melt quality tantalum core 30 and a Pt—Ir cladding 32. Cladding 32 has a maximum thickness of approximately one micron.

While the present disclosure describes the application of to Pt—Ir cladding to a melt quality tantalum core, the inventors believe that the present invention may also be practiced using a tantalum core having a finer grain size such as the sintered tantalum core wires discussed above.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

In the foregoing detailed description, the invention has been described with reference to specific embodiments. However, it may be appreciated that various modifications and changes can be made without departing from the scope of the invention as set forth in the appended claims.

The invention claimed is:

1. An implantable electrode lead for electrical stimulation of a body, comprising:
an elongated insulative lead body;
a conductor within the lead body; and
an electrode coupled to the conductor comprising a coiled wire comprising a platinum-iridium cladding directly overlaying an un-smoothed melt quality tantalum core, the cladding forming an exposed surface of the electrode and having a maximum thickness of less than three microns.

2. An implantable lead according to claim 1 wherein the maximum thickness of the cladding is one micron.

3. An implantable lead according to claim 2 wherein the cladding of about 1 micron does not expose the melt quality tantalum core.

4. An implantable lead according to claim 1 wherein the maximum thickness of the cladding is two microns.

5. A method of producing an implantable electrode lead for electrical stimulation of a body of the type comprising an elongated insulative lead body, a conductor within the lead body; and an electrode coupled to the conductor, comprising:
   including as the electrode a coiled wire comprising a platinum-iridium cladding directly overlaying an un-smoothed melt quality tantalum core, the core wire cladding forming an exposed surface of the electrode and having a maximum thickness of less than three microns.

6. A method of producing an implantable electrode lead for electrical stimulation of a body of the type comprising an elongated insulative lead body, a conductor within the lead body and an electrode coupled to the conductor, comprising:
   employing Anomet, Inc to apply a platinum-iridium cladding to a tantalum core to produce an electrode wire in which the cladding forms an exposed surface of the electrode having a maximum thickness of less than three microns; and
   coiling the wire to form the electrode and further comprising mounting the coiled wire electrode extending outward from the insulative lead body.

7. A method according to claim 6 comprising mounting the conductor within the lead body extending proximally from the coiled wire electrode.

8. A method according to claim 7 wherein the coiled wire electrode is an exposed distal portion of the conductor.

9. A method according to claim 7 wherein the coiled wire electrode is coupled to the conductor by a crimp joint and/or a weld joint.

* * * * *